US008282278B2

(12) United States Patent
Sharpless

(10) Patent No.: US 8,282,278 B2
(45) Date of Patent: Oct. 9, 2012

(54) GANTRY COOLING

(75) Inventor: Ronald B. Sharpless, Cleveland, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 395 days.

(21) Appl. No.: 12/742,754

(22) PCT Filed: Nov. 4, 2008

(86) PCT No.: PCT/IB2008/054594
§ 371 (c)(1),
(2), (4) Date: May 13, 2010

(87) PCT Pub. No.: WO2009/069024
PCT Pub. Date: Jun. 4, 2009

(65) Prior Publication Data
US 2010/0266096 A1 Oct. 21, 2010

Related U.S. Application Data

(60) Provisional application No. 60/991,233, filed on Nov. 30, 2007.

(51) Int. Cl.
*H01J 35/10* (2006.01)

(52) U.S. Cl. ............................................ 378/199; 378/4

(58) Field of Classification Search ................ 378/4–20, 378/199, 141
See application file for complete search history.

(56) References Cited

U.S. PATENT DOCUMENTS

| | | | | |
|---|---|---|---|---|
| 5,610,968 | A * | 3/1997 | Deucher et al. | 378/199 |
| 5,761,269 | A * | 6/1998 | Sugihara et al. | 378/199 |
| 6,276,145 | B1 | 8/2001 | Sharpless et al. | |
| 6,404,845 | B1 | 6/2002 | Sharpless et al. | |
| 6,909,775 | B2 | 6/2005 | Ray et al. | |
| 7,023,952 | B2 | 4/2006 | Brunnett | |
| 7,201,515 | B2 | 4/2007 | Lacey | |
| 2004/0202287 | A1 | 10/2004 | Muller | |
| 2004/0228450 | A1* | 11/2004 | Mueller | 378/199 |
| 2005/0287008 | A1 | 12/2005 | Lacey et al. | |
| 2006/0109956 | A1 | 5/2006 | Lacey | |
| 2006/0126782 | A1 | 6/2006 | Pohan et al. | |
| 2006/0215808 | A1* | 9/2006 | Lacey | 378/19 |
| 2007/0098137 | A1* | 5/2007 | Joshi et al. | 378/19 |

* cited by examiner

Primary Examiner — Hoon Song

(57) ABSTRACT

A medical imaging apparatus (100) includes a rotating gantry (302). The rotating gantry (302) includes a first side (108) and a second side (302, 304). The first and second side (108 and 302, 304) are spaced apart from each other along a longitudinal axis, thereby defining a plenum (116) therebetween. The first side (108) includes at least one material free region (110). At least one air mover (126), located in the plenum (116), that expels air in the plenum (116) through the at least one material free region (110).

20 Claims, 3 Drawing Sheets ic CT suspension."

GANTRY COOLING

CROSS REFERENCE TO RELATED APPLICATIONS

This application claims the benefit of U.S. provisional application Ser. No. 60/991,233 filed Nov. 30, 2007, which is incorporated herein by reference.

The present application relates to a medical imaging system gantry, and finds particular application to computed tomography (CT). However, it also amenable to other medical imaging applications and to non-medical imaging applications.

A computed tomography (CT) scanner has included a stationary gantry and a rotating gantry. The stationary gantry is stationary in that it is generally stationary during scanning. However, the stationary gantry may be configured to tilt and/or otherwise be moved. The rotating gantry is rotatably coupled to the stationary gantry and rotates around an examination about a longitudinal or z-axis. With a third generation system, an x-ray tube and a radiation sensitive detector array are affixed to the rotating gantry on opposite sides of the examination region and rotate with the rotating gantry around the examination region. Radiation emitted by the x-ray tube traverses the examination region and illuminates the radiation sensitive detector array. Other imaging and electrical components are affixed to the rotating gantry.

During scanning, some of the components of the scanner such as the x-ray tube generate and dissipate heat. This heat may result in temperature fluctuations in the ambient temperature in the scanner. Unfortunately, the electronics, the detector array, and/or other components of the scanner may be temperature sensitive. As such, a temperature fluctuation in the ambient temperature in the scanner may undesirably affect one or more of the components of the scanner and, thus, the performance of the scanner. Changes in the room temperature may likewise lead to undesired temperature fluctuations in the ambient temperature in the scanner.

Scanner component cooling techniques have been implemented. For instance, a fan has been placed on the side of the rotating gantry to which a temperature sensitive component is affixed and next to the temperature sensitive component. However, such a fan re-circulates the air in the scanner. As a consequence, when the temperature of the air in the scanner increases due to heat dissipation from heat generating components, the heated air is re-circulated over the temperature sensitive component.

In another instance, a fan located in the stationary gantry draws air into a region near the bottom of the scanner, and a vent allows heated air to leave through the top of the scanner. Unfortunately, this may lead to an uneven temperature distribution in the air in the scanner. For example, this may lead to a cooler temperatures near the bottom of scanner and warmer temperatures near the top of the scanner. As a result, the rotating temperature sensitive components, as they rotate, see air having a temperature that is dependent on the angular location of the rotating temperature sensitive component. As such, the temperature of the air at a component may not be readily predicable.

In another instance, air having a substantially constant temperature is distributed to various regions and temperature sensitive components. Unfortunately, for a given pressure, the flow of air to a region or a temperature sensitive component is generally constant, and heat may be more efficiently dissipated by otherwise providing the flow of air.

Aspects of the present application address the above-referenced matters and others.

According to one aspect, a medical imaging apparatus includes a rotating gantry. The rotating gantry includes a first side and a second side. The first and second side are spaced apart from each other along a longitudinal axis, thereby defining a plenum therebetween. The first side includes at least one material free region. At least one air mover, located in the plenum, expels air in the plenum through the at least one material free region.

According to another aspect, a medical imaging method includes drawing air into a plenum of a rotating gantry of a medical imaging apparatus with an air mover that is located in the plenum. The method further includes expelling the air in the plenum into a region of the medical imaging apparatus with the air mover.

According to another aspect, a rotating gantry of a medical imaging apparatus includes a bearing and a rotor. The rotating gantry and the bearing are coupled. The rotating gantry and the bearing are spaced apart from each other by a non-zero distance, thereby defining a plenum therebetween. An air mover, located in the plenum, draws air into the plenum and expels air out of the plenum.

The invention may take form in various components and arrangements of components, and in various steps and arrangements of steps. The drawings are only for purposes of illustrating the preferred embodiments and are not to be construed as limiting the invention.

Figure 6:
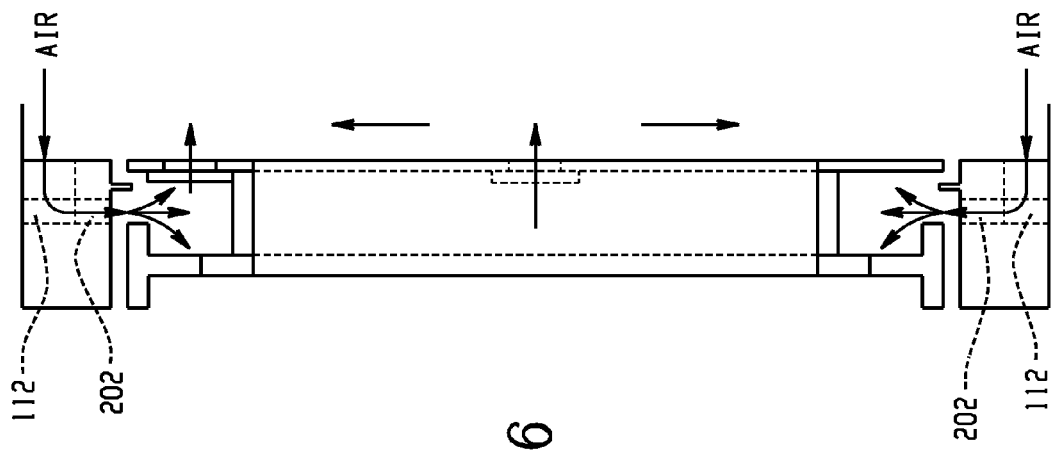
Figure 4:
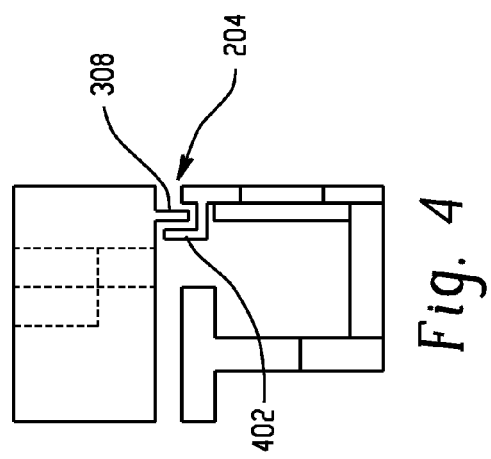
Figure 5:
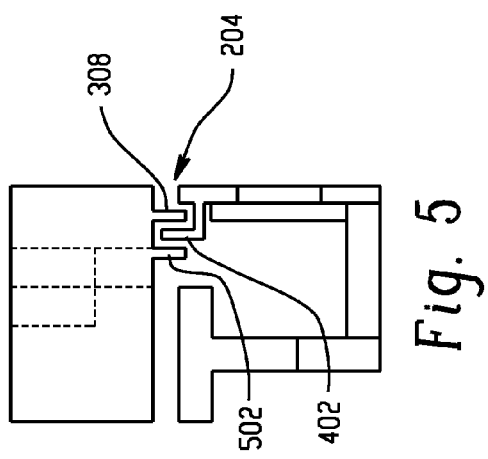

FIGS. 4, 5, and 6 illustrate sectional views showing alternative embodiments.

Figure 1:
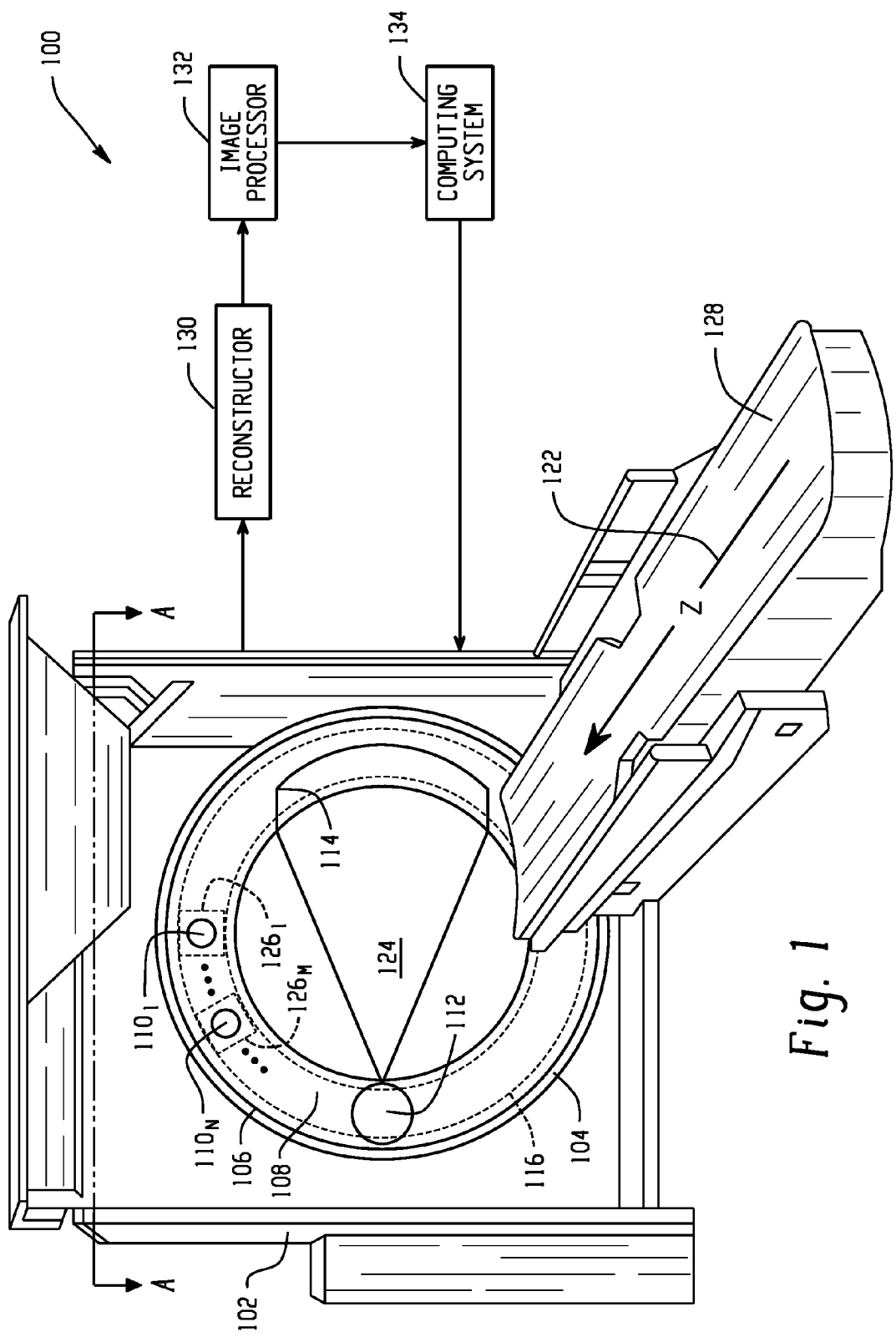
FIG. 1 illustrates a medical imaging apparatus.

Initially referring to FIG. 1, a computed tomography (CT) scanner 100 includes a stationary gantry 102, which is stationary in the sense that it is generally stationary during scanning. However, the stationary gantry 102 may be configured to tilt and/or otherwise be moved. The stationary gantry 102 includes a generally annular aperture 104.

The scanner 100 also includes a generally annular rotating gantry 106. In the illustrated embodiment, the rotating gantry 106 includes various components such as a rotor 108, a slip ring 304 (FIG. 3), a data ring 306 (FIG. 3), and/or other components. The rotor 108 includes one or more material free regions $110_1 \ldots 110_N$. Heat generating and/or sensitive components such as a radiation source 112, a radiation sensitive detector array 114, and/or other components are affixed to the rotor 108 in regions near the one or more material free regions 110. A fourth generation CT configuration is also contemplated.

The rotating gantry 106 is rotatably coupled to the stationary gantry 102 via a bearing 302 (FIG. 3) and rotates about a z-axis 122 around an examination region 124. A suitable bearing includes a mechanical bearing, such as one with rolling balls interposed between two raceways, a fluid bearing, such as an air bearing that provides an air barrier between the rotating gantry 106 and the stationary gantry 102, and/or other bearings. An example of a suitable fluid bearing is described in patent application Ser. No. 09/428,431, filed Oct. 27, 1999, and entitled "Aerostatic CT suspension."

In non-limiting embodiment, the physical arrangement of the bearing with respect to the rotating gantry 106 defines a plenum 116. As described in greater detail below, air from the plenum 116 traverses the one or more material free regions 110 of the rotor 108. This air, based on its temperature, may increase or decrease the temperature of the air in the scanner 100 and, hence, one or more of the components of the scanner 100. As a result, the air in the plenum 116 can be temperature conditioned and employed to regulate the temperature of the air and/or components in the scanner 100. To facilitate this, one or more air movers $126_1$ and $126_M$, such as fans, can be used to selectively distribute the air in the plenum 116 through the material free regions 100 to one or more components on the rotor 108 and/or regions in the scanner 100. One or more of the air movers 126 may be selectively controlled. Such control may include individually turning an air mover 126 on and off and/or individually setting the speed of an air mover 126.

The radiation source 112 emits radiation that traverses the examination region 124. The radiation sensitive detector array 114, which subtends an angular arc on a side of the examination region 124 opposite the radiation source 112, detects radiation that traverses the examination region 124. The detector array 114 includes multiple rows of radiation sensitive detector elements that extend in the z-axis direction, and multiple columns of radiation sensitive detector elements that extend in a traverse direction. A single row detector array configuration is also contemplated.

A patient support 128, such as a couch, supports a patient in the examination region 124. The patient support 128 is movable along the z-axis 122 in coordination with the rotation of the rotating gantry 106 to facilitate helical, axial, or other desired scanning trajectories.

A reconstructor 130 reconstructs projection data from the detectors to generate volumetric data indicative of the interior anatomy of the patient. An image processor 132 processes the volumetric image data generated by the reconstructor 130 for display in human readable form.

A general purpose computing system 134 serves as an operator console. The operator console 134 includes human readable output devices such as a display and/or printer and input devices such as a keyboard and/or mouse. Software resident on the console 134 allows the operator to control the operation of the system 100, for example, by allowing the operator to select a scan protocol, initiate scanning, terminate scanning, view and/or manipulate the volumetric image data, and/or otherwise interact with the system 100.

Figure 2:
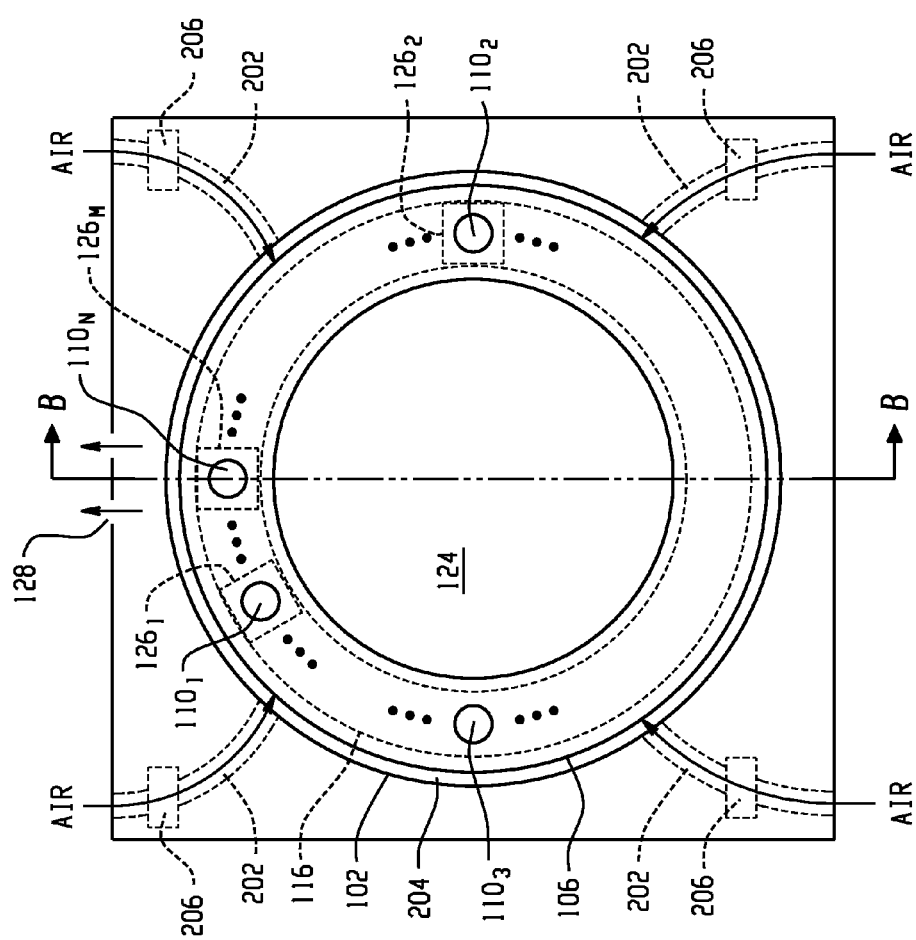
FIG. 2 illustrates a first sectional view of the medical imaging apparatus.

FIG. 2 illustrates a sectional view of the scanner 100 of FIG. 1 along A-A. In this view, two additional material free regions $110_2$ and $110_3$ are shown. Note that the material free region $110_2$ is located in a region of the rotor 108 configured to receive the detector array 114, and the material free region $110_3$ is located in a region of the rotor 108 configured to receive the radiation source 112.

The illustrated location, size, shape and number of material free regions 110 is provided for explanatory purposes. In other embodiments, the location, size, shape and/or number of the material free regions 110 may differ. For example, in one non-limiting embodiment the location, size, and/or shape of a material free region 110 provides suitable air flow for maintaining or regulating the temperature of a component located in a region in which the air flows within a preset range of temperatures.

Inlets 202, such as intake ducts, are configured to receive air from the atmosphere around the stationary gantry 102. As shown, the inlets 202 extend through the stationary gantry 102 to an air gap 204 between the stationary gantry 102 and the rotating gantry 106. Similarly, the illustrated location, size, shape and number of the inlets 202 is provided for explanatory purposes, and, in other embodiments, the location, size, shape and/or number of the inlets 202 may differ.

Respective filters 206 filter the air that flows through the inlets 202.

An air mover $126_2$ expels air in the plenum 116 through the material free region $110_2$. Air pressure in the plenum 116 expels air through the material free region $110_3$. The air mover $126_1$ and $126_M$ expel air in the plenum 116 through the material free regions $110_1$ and $110_N$.

One or more outlets 208, such as a vent, allow air to flow between the scanner 100 and the atmosphere around the scanner 100. Similarly, the illustrated location, size, shape and number of the one or more outlets 208 is provided for explanatory purposes, and, in other embodiments, the location, size, shape and/or number of the one or more outlets 208 may differ.

Figure 3:
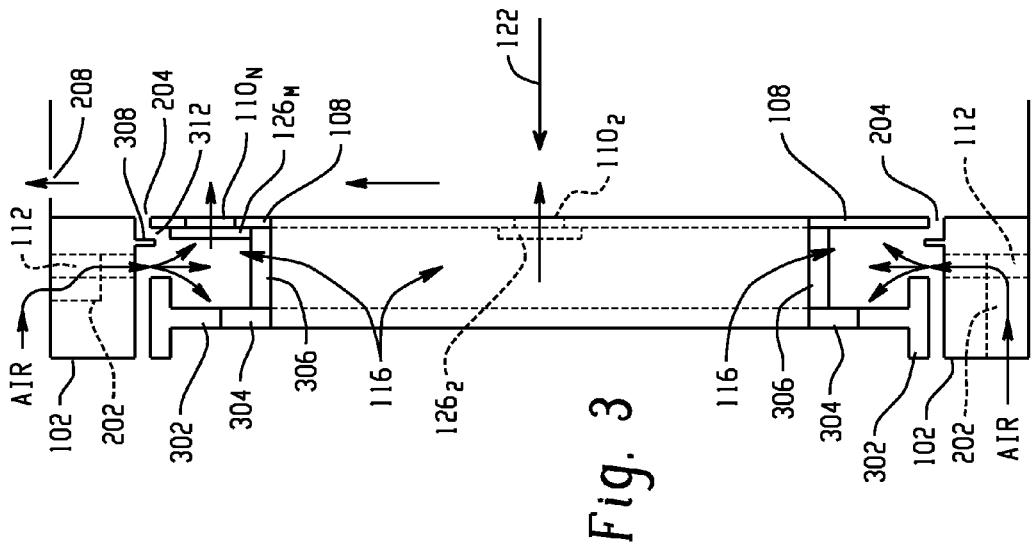
FIG. 3 illustrates a second sectional view of the medical imaging apparatus.

FIG. 3 illustrates a sectional view of the scanner 100 of FIG. 2 along B-B. It is noted that the size of some of the components shown in FIG. 3 have modified for explanatory purposes. In the illustrated embodiment, the bearing 302 is generally "T" shaped and is coupled to the rotor 108 through the slip ring 304 and the data ring 306. In other embodiments, the bearing 302 may be alternatively shaped and/or the bearing 302 and the rotor 108 may be otherwise coupled. As noted above, the location of the bearing 302 with respect to the rotor 108 defines the plenum 116 therebetween, for example with the rotor 108 being at least part of a side of the plenum and the bearing 302 being at least part of a side of the plenum. In the illustrated embodiment, the recess of the "T" on the side of the plenum 116 is part of the plenum 116.

With respect to FIGS. 1-3, it is to be appreciated that the size and/or shape of each material free regions 110 may vary with respect to the other material free regions 110. In one instance, the size and/or shape of at least one of the material free regions 100 provides a suitable amount of air to a region such that the temperature of at least one component in the region is maintained within a preset range of temperatures. Additionally or alternatively, the speed of an air mover 126 provides a suitable amount of air to a region such that the temperature of at least one component in the region is maintained within a preset range of temperatures.

Referring again to FIG. 3, the stationary gantry 102 and the rotor 108 are separated by the gap 204. The stationary gantry 102 includes a protrusion 308 that extends towards the plenum 116 through a height of the gap 204 and is positioned between the bearing 302 and the rotor 108. The protrusion 308 is separated from the rotor 108 by a second gap 312. The gaps 204 and 312 combine to define a path between the plenum 116 and a side of the rotor 108 on which are affixed the radiation source 112 and the detector array 114. In one non-limiting example, the gap 204 has a height of about five (5) millimeters (mm), the second gap 312 has a height of about one (1) millimeters (mm), and the gaps 204 and 312 combine to defined a path with a length about nine (9) mm.

The volume of air in the plenum 116 that leaks through the path may vary based on the height of the gaps 204 and 312, and the length and shape of the path. In the illustrated embodiment, the height of the gaps 204 and 312, and the length and shape of the path are such that the temperature and pressure of the air in the plenum 116 is substantially constant and predictable. The height of the gaps 204 and 312, and the length and shape of the path may also reduce the volume of air leakage relative to embodiments that do not include the protrusion 308. A result of reducing the air leakage from the path includes decreased load on the air movers 126 with respect to a substantially similar plenum air pressure. Other results are also contemplated.

FIGS. 4 and 5 show alternative embodiments in which the length and shape of the path defined by the gaps 204 and 312 can be configured to further reduce air leakage from the plenum 116. In FIG. 4, the rotor 108 includes a generally "L"

shape protrusion 402. As shown, the protrusion 402 extends towards the stationary gantry 102 through the gap 204 and is positioned between the bearing 302 and the protrusion 308, forming a two turn path. In FIG. 5, the rotor 108 includes the protrusion 402, the stationary gantry 102 includes the protrusion 308, and a second protrusion 502, which extends towards the plenum 116 through the gap 204 and is positioned between the bearing 302 and the protrusion 402 of the rotor 108. The protrusions 308 and 502 define a generally "U" shaped region, and a leg of the generally "L" shaped protrusion 402 lies between the legs of the "U" shaped region, forming a three turn path. Additional protrusions are contemplated.

Variations are described.

In the illustrated embodiment, the filters 206 are included in inlet path 202. In another embodiment, an air cooling device such as a heat exchanger is used in conjunction with the inlets 202. For example, in one instance a heat exchanger is positioned at the entrance of an inlet 202. As such, the air is cooled prior to traversing the inlet 202. In another instance, the heat exchanger may be placed within the inlet path.

In another embodiment, an air heating device such as a heater is used in conjunction with the inlets 202. For example, in one instance a heater is positioned at the entrance of an inlet 202. As such, the air is heated prior to traversing the inlet 202. In another instance, the heater may be place within the inlet path.

In the illustrated embodiment, the air movers 126 are located between the bearing 302 and the rotor 108. In another embodiment, at least one of the air movers 126 is located on a side of the rotor 108 outside of the plenum 116. Additionally or alternatively, at least one of the air movers 126 is located in the path of at least one of the inlets 202. Additionally or alternatively, at least one air mover is used to expel air in the scanner 100 out of the outlet 208.

In another embodiment, a controller of the scanner 100 is used to control one or more of the air movers 126. In one instance, the controller controls at least one of the air movers 126 based on scanning parameters. For example, based on the tube power, an estimated time duration of the scan, and/or other parameters, the controller estimates the temperature in the scanner 100 and controls the speed of the air movers to maintain a preset temperature range in the scanner 100.

In another embodiment, a temperature measurement system measures the air temperature in the scanner 100, and the controller controls the one or more of the air movers 126 based on the measured air temperature. Such a measurement can be continuously, periodically, aperiodically, or otherwise performed.

In another embodiment, the temperature measurement system may additionally or alternatively measures the air temperature of one or more of the components, and the controller controls the one or more of the air movers 126 based on the measured temperature(s). Again, such a measurement can be continuously, periodically, aperiodically, or otherwise performed FIGS. 2-5 show an open system in which air from the atmosphere around the scanner 100 enters the inlets 202, and the air in the scanner 100 exits the scanner 100 through the one or more outlets 208. FIG. 6 illustrates a closed system. As shown, with a closed system, the air in the scanner 100 is recycled back through the inlets 202 rather than being expelled into the atmosphere around the scanner 100 is located.

In operation, one or more of the air movers 126 are turned on. This may occur before, during and/or after performing a scan. In addition, the number of air movers 126 turned on and/or the speed at which individually air movers 126 are operated may be based on various factors as discussed above. These air movers 126 create suction in the plenum 116, which draws in air from around the perimeter of the scanner 100 into the inlets 202. The air is conditioned and traverses the inlets 202 to the gap 402. The air then enters the plenum 116. The turned on air movers expel the air in the plenum to various regions of the scanner based on the location of the material free regions 110 in the rotor 108. The expelled air facilitates maintaining preset temperature range of the scanner 100. For instance, the expelled air may transfer heat away from or to various components of the scanner 100, depending on whether the expelled air is colder or hotter than the temperature in the scanner 100. The air in the scanner 100 leaves through the outlet 208.

The embodiments herein were described in connection with a computed tomography medical imaging applications. However, it is to be understood that the invention may additionally or alternatively be employed with other medical imaging applications and/or non-medical imaging applications in which it is desirable to regulate temperature.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A medical imaging apparatus, comprising:
   a rotating gantry, including:
      a first side; and
      a second side, wherein the first and second side are spaced apart from each other along a longitudinal axis, thereby defining a plenum therebetween, and the first side includes at least one material free region; and
      at least one air mover located in the plenum, wherein the at least one air mover expels air in the plenum through the at least one material free region.

2. The medical imaging apparatus of claim 1, wherein the at least one air mover is affixed to the first side between the second side and the at least one material free region.

3. The medical imaging apparatus of claim 2, further including a temperature sensitive component, wherein the temperature sensitive component is affixed to the first side on a region outside of the plenum (116) opposite the at least one air mover.

4. The medical imaging apparatus of claim 3, wherein the expelled air transfers heat away from the temperature sensitive component.

5. The medical imaging apparatus of claim 3, wherein the temperature sensitive components includes a radiation source or a radiation detector array.

6. The medical imaging apparatus of claim 2, further including a controller that varies a speed of the at least one air mover during scanning based on the temperature of the temperature sensitive component.

7. The medical imaging apparatus of claim 1, wherein the first side includes a rotor and the second side includes a bearing, and at least a sub-portion of the plenum is located between the rotor and the bearing.

8. The medical imaging apparatus of claim 7, wherein the is part of an air bearing.

9. The medical imaging apparatus of claim 1, further including:

a stationary gantry wherein the rotating gantry is rotatably coupled to the stationary gantry; and at least one air inlet, wherein the at least one air inlet extends through the stationary gantry from an outer surface of the stationary gantry to the rotating gantry.

10. The medical imaging apparatus of claim 9, wherein air from the atmosphere outside of the stationary gantry or air from within the stationary gantry flows through the air inlet to the plenum.

11. The medical imaging apparatus of claim 10, wherein the at least one air mover creates suction in the plenum that pulls air into and through the air inlet to the plenum.

12. The medical imaging apparatus of claim 9, the rotating gantry further including a rotor, wherein the rotator and the stationary gantry are physically radially separated from each other in a direction perpendicular to the longitudinal axis, thereby forming a gap therebetween, and the stationary gantry further including at least one protrusion that extends through a height of the gap in a direction towards the plenum.

13. The medical imaging apparatus of claim 12, wherein the at least one protrusion inhibits air from moving from inside the plenum through the gap to outside of the plenum.

14. The medical imaging apparatus of claim 1, wherein the medical imaging system is computed tomography system.

15. A medical imaging method, comprising:

drawing air into a plenum of a rotating gantry of a medical imaging apparatus with an air mover located in the plenum;

expelling the air in the plenum into multiple regions of the medical imaging apparatus with the air mover.

16. The method of claim 15, wherein the expelled air maintains a temperature of the region.

17. The method of claim 15, wherein at least one temperature sensitive component of an imaging portion of the medical imaging apparatus is located in the region, and wherein the expelled air facilitates transferring heat away from the at least one temperature sensitive component.

18. The method of claim 15, wherein the plenum is defined by a space between a bearing and a rotor of the rotating gantry.

19. A rotating gantry of a medical imaging apparatus, comprising:

a bearing;

a rotor coupled to the bearing, wherein the bearing and rotor are spaced apart from each other by a non-zero distance, thereby defining a plenum therebetween; and an air mover located in the plenum, wherein the air mover draws air into the plenum and expels air out of the plenum.

20. The rotating gantry of claim 19, wherein the expelled air regulates a temperature of at least one electronic component affixed to the rotor.

* * * * *